US006293293B1

United States Patent
Wrigley et al.

(10) Patent No.: US 6,293,293 B1
(45) Date of Patent: Sep. 25, 2001

(54) VALVE

(75) Inventors: Andrew Nicholson Wrigley; Tomislav Govorko, both of Auckland (NZ)

(73) Assignee: ITW New Zealand Limited, Auckland (NZ)

(*) Notice: Subject to any disclaimer, the term of this patent is extended or adjusted under 35 U.S.C. 154(b) by 0 days.

(21) Appl. No.: 09/310,370

(22) Filed: May 12, 1999

(30) Foreign Application Priority Data

May 12, 1998 (NZ) ........................................... 329181

(51) Int. Cl.[7] ................................ F16K 1/38; F16L 29/02
(52) U.S. Cl. ........................... 137/1; 251/149.1; 251/339; 137/614.04
(58) Field of Search ................................ 251/149.1, 339, 251/331; 137/843, 68.14, 67, 614.04, 1; 604/249, 905

(56) References Cited

U.S. PATENT DOCUMENTS

| 3,463,452 | * | 8/1969 | Nilsen et al. ................. 251/339 X |
| 4,169,548 | * | 10/1979 | Bond ........................... 251/339 X |
| 4,387,879 | * | 6/1983 | Tauschinski .................. 251/149.1 |
| 5,046,645 | * | 9/1991 | Hagan et al. .................. 251/149.1 |
| 5,163,922 | * | 11/1992 | McElveen, Jr. et al. ........ 251/149.1 |
| 5,211,638 | * | 5/1993 | Dudar et al. .................. 604/283 |
| 5,215,538 | * | 6/1993 | Larkin ........................... 251/149.1 |
| 5,251,873 | * | 10/1993 | Atkinson et al. .............. 251/149.1 |
| 5,280,876 | * | 1/1994 | Atkins ........................... 251/149.1 |
| 5,289,849 | * | 3/1994 | Paradis .......................... 251/149.1 X |
| 5,395,348 | * | 3/1995 | Ryan .............................. 251/149.1 X |
| 5,462,255 | * | 10/1995 | Rosen et al. ................... 251/149.1 |
| 5,465,938 | * | 11/1995 | Werge et al. .................. 251/149.1 |
| 5,487,728 | * | 1/1996 | Vaillancourt .................. 604/86 |
| 5,509,433 | * | 4/1996 | Paradis .......................... 137/843 |
| 5,535,771 | * | 7/1996 | Purdy et al. ................... 251/149.1 X |
| 5,540,661 | * | 7/1996 | Tomisaka et al. ............. 251/149.1 X |
| 5,569,235 | * | 10/1996 | Ross et al. .................... 251/149.1 X |
| 5,578,059 | * | 11/1996 | Patzer ........................... 251/149.1 X |
| 5,676,346 |   | 10/1997 | Leinsing . |
| 5,730,418 | * | 3/1998 | Feith et al. .................... 251/149.1 X |

FOREIGN PATENT DOCUMENTS 0 432 070 B1   7/1994  (EP) .

* cited by examiner

Primary Examiner—John Rivell
(74) Attorney, Agent, or Firm—Lowe Hauptman Gilman & Berner, LLP

(57) ABSTRACT

The present invention is capable of engagement with a fluid port and capable of being open to create a fluid path, where the valve assembly includes a valve head for closing a fluid path to a port associated with a valve assembly, and a housing, and at least one engagement element formed integrally with the housing, wherein the valve assembly is characterized in that to open the valve assembly the valve head is driven into an engagement element deforming the valve head and creating the fluid path through the valve assembly.

12 Claims, 2 Drawing Sheets

VALVE

TECHNICAL FIELD

This invention relates to improvements in and associated with valves, valve seals and their methods of manufacture.

BACKGROUND ART

Reference throughout this specification shall now be made to the present invention being used in fluid transfer applications. However, it should be appreciated by those skilled in the art that the present invention may be employed in other applications, not necessarily being just the transfer of fluid. For example, the present invention may be employed to allow the transfer of a fine particulate material such as a powder.

Valves are used in numerous applications to control the flow of a fluid from one point or container to another point or container. Valve assemblies are preferably manufactured from plastic materials as this reduces manufacturing cost and time, allowing a large number of valve assemblies to be produced with a high degree of conformity in shape and quality.

When moulding plastic material into the components of a valve it is desirable that the number of individual parts employed is minimised. If the majority of a valve assemblies components could be moulded from one single component this is of great advantage.

As the number of separate components employed increases so does:

a) the number of separate tools required in the manufacturing process, increasing the capital start up costs for the manufacturer and associated manufacturing costs, and b) a slow down in the manufacturing process time as a large number of components need to be firstly formed and finished and then assembled together to form the finished product, and c) an increase in the amount of waste material generated in the manufacturing process as a consequence of the increase in the number of parts formed.

For example, in one instance when a valve assemble must include a separate latch component the cost of manufacturing and its associated process time increases.

In some instances where separate components are required in a valve assembly, collapsible cores within the moulds are required. These collapsible cores enable undercuts to be formed within the components manufactured, and are typically used to construct threads on bottles. Each of the cores required are expensive to purchase and to also fit into the manufacturing machinery.

The number of parts employed in a valve assembly can also be minimised by using "snap fit" assembly techniques. Components can be retained in place in the valve assembly by using complimentary shapes which when pushed or 'snapped' together will hold the components in place.

A valve which could be manufactured from plastic material and which also could be assembled as a "snap fit" without any additional adhesives or attachment components would be of great advantage to the manufacturer. A "snap fit" assembly process again reduces the number of components of the valve and hence will also reduce the manufacturing time associated with assembling the valve.

A valve that solved any or all of the above problems would be a great advantage over the prior art. Specifically a valve which could be manufactured from plastic materials, which incorporated a minimum number of separate components and which could be "snap fit" assembled together would be of great advantage over the prior art.

It is an object of the present invention to address the foregoing problems or at least to provide the public with a useful choice.

Further aspects and advantages of the present invention will become apparent from the ensuing description that is given by way of example only.

DISCLOSURE OF INVENTION

According to one aspect of the present invention there is provided a valve assembly capable of engagement with a fluid port and capable of being opened to create a fluid path, where the valve assembly includes, a valve head for closing a fluid flow path to a fluid port associated with the valve assembly, a housing, at least one engagement element formed integrally with the housing, the valve assembly characterised in that to open the valve assembly the valve head is driven into an engagement element, deforming the valve head and creating a fluid path through and the valve assembly.

According to another aspect of the present invention there is provided a method of constructing a valve assembly substantially as described above, the method of construction characterised by the step of integrally forming at least one engagement element in the housing during construction of the valve assembly.

According to yet another embodiment of the present invention there is provided a valve assembly that includes an elastically resilient valve head located within a housing, whereby movement of the valve head within the housing causes the valve head to deform and open or close the valve assembly. According to a further aspect of the present invention there is provided a method of opening a valve assembly characterised by the steps of (a) forcing a valve head against an engagement element, and (b) deforming at least a portion of the valve head against the engagement element, and (c) creating a fluid path through the valve assembly past the deformed valve head.

A valve assembly may be defined as any arrangement of a number of components with two configurations, being an open configuration and a closed configuration. In a closed configuration, the valve assembly (when associated with a fluid port) will prevent fluid flowing from the fluid port into one end of the valve assembly and out of another end of the valve assembly. In an open configuration the valve assembly will allow fluid to flow from an associated fluid port into the valve assembly and out another end of the valve assembly.

In a preferred embodiment where the valve assembly is capable of engagement with a fluid port, the valve assembly may include a connector to facilitate engagement between the two elements. Such a connector (formed for example by a tube or hose) could engage the valve assembly with a fluid port, ensuring fluid can flow from one to the other and also that fluid does not leak out through the connector and away from either the valve assembly or fluid port.

Reference throughout this specification being made to the present invention being used in conjunction with fluids and facilitating the creation of a fluid path. The term "fluid" may be defined as any type of material that can flow relatively easily through a path created in a valve assembly. For example, a fluid may consist of a gas, liquid or a fine particulate powder. Further, the term fluid path is used to describe a channel or guide through which a fluid may travel.

In a preferred embodiment the valve head may include an elastically deformable cup mounted on the end of a substantially straight stem. It is envisioned that in this embodiment the deformable cup will have approximately twice the diameter of the stem to extend out well past the edges of the stem.

Alternative embodiments of the present invention may not employ an elastically deformable cup mounted on a straight stem as the valve head. For example, a single elastic component or any other combination of elastically deformable component may be employed as the valve head. Any type of componentry can be used which can easily deform to create a fluid path after being driven into an engagement member and then afterwards allow the original shape of the component to return, closing the fluid path.

Reference throughout this specification shall now be made to the valve head as being an elastically deformable cup mounted on a semi-ridged straight valve stem. However, it should be appreciated by those skilled in the art that other forms of valve head may be used in conjunction with the present invention and reference to the above should in no way be seen as limiting.

It is envisioned in a preferred embodiment that the cup end of the valve head will be used to cover and close a section of the fluid path normally formed through the valve assembly. Once the cup is deformed a fluid path is created around the deformed sides of the cup, allowing fluid to flow through the valve assembly around and past the valve head stem. The valve may be closed by relaxing the force driving the valve head cup into an engagement element, allowing the cup to reform to its original shape and close the fluid path through the valve assembly.

In a preferred embodiment the elastically deformable valve head cup may be constructed from an elastic yet resilient material. This material will allow the cup to be deformed, creating a fluid path around the sides of the cup, and yet allow the cup to reform back into its original shape once it is no longer being driven against an engagement indentation.

In a preferred embodiment of the present invention the valve head stem may also include protrusions along its length. Such protrusions may be positioned to keep the valve head in position within the housing. For example, in one embodiment protrusions may be included in the valve stem to prevent the valve head from travelling down through the valve assembly away from the housing's engagement indentations.

In a preferred embodiment the valve assembly housing may be an element which forms the outer body of the valve assembly and includes a hollow channel substantially near the center of the valve assembly through which fluid may flow. Preferably, the housing also includes a cavity in its interior into which the valve head may be positioned.

It is envisioned that in preferred embodiments the valve assembly only includes two separate components, being the valve head and the housing with at least one integrally formed engagement element. As discussed earlier, configuring the valve assembly in this manner reduces the manufacturing cost and time associated with producing the valve assembly.

In a preferred embodiment an engagement element formed integrally with the housing consists of an indentation in the inner surface of the housing, which allows the edge of the valve head cup to sit inside the indentation, seating an edge of the cup on the forward edge of the engagement elements wall. This type of engagement element securely positions the valve head inside the housing, locking it in place in the engagement element indentation so that a knock or bump will not push the valve head out of position, which can permanently create a fluid path through the valve assembly.

An indentation may be defined as any type of recess or aperture located in the body of the valve assembly housing.

In this embodiment the forward edge of the valve head cup will sit inside the engagement element indentation. When the valve head is forced into the edge of the engagement indentation the valve head cup will deform creating a fluid path around the deformed side.

In a further preferred embodiment the housing includes four integrally formed engagement indentations positioned evenly around the sides of the housing. These four engagement indentations securely position the valve head cup within the housing and also ensure that the valve head cup is deformed equally on all sides, preventing the valve head cup from being "popped" out of place when driven into the engagement indentation.

Reference throughout this specification will now be made to the engagement elements being indentations, holes or recesses formed within the housing of the valve assembly. Those skilled in the art should appreciate that other configurations of the valve assembly and engagement elements are considered and reference to the above only throughout this specification should in no way be seen as limiting.

Reference throughout the specification will also now be made to the valve assembly as including four engagement elements. However, it should be appreciated by those skilled in the art that any number of engagement elements can be used in conjunction with the present invention, and reference to four elements should in no way be seen as limiting.

Alterative embodiments of the present invention may not employ an indentation in the housing inner surface as an engagement element. For example, in alternative embodiments protrusions moulded into the inner surface of the housing may be employed as engagement elements. Such protrusions may catch and hold one edge of the valve head cup, deforming the cup as a force is applied to move the cup into the engagement protrusion.

Reference throughout this specification shall now be made to the engagement elements as being indentations. However, it should be appreciated by those skilled in the art that other forms of engagement element may be used in conjunction with the present invention, and reference to the above should in now way be seen as limiting.

In a preferred embodiment all the engagement elements used in the present invention are integrally formed into the housing, making the housing combined with the engagement indentations a single component. This feature of the invention ensures that a valve assembly may be constructed from the minimum number of separate components and also allows the engagement indentations to firmly seat the valve head inside the valve housing.

In a preferred embodiment the valve head may be driven or forced against an engagement member via a force applied to the end of the valve stem. The valve stem may be forced forward, forcing the valve head cup to deform against an engagement indentation and create a fluid path through the valve assembly.

In a further preferred embodiment it is envisioned that two valve assemblies may be linked together at either end of a fluid passage, to allow fluid to be transferred across the fluid passage. In such an embodiment the fluid passage may include a pusher rod at approximately the centre of the passage which may engage either end of either valve assembly's valve head stems. This pusher rod may force both valve stems and associated valve heads further into each valve assembly, opening a fluid path in each valve assembly and allowing fluid to flow from one valve assembly, though the fluid channel, and out through the second valve assembly.

This second valve assembly may be defined as a connector. This connector may have similar features to the present invention, including a snap fit together construction and may be designed to avoid the requirement of an 0-ring seal, as in the present invention.

The present invention provides many advantages over existing prior art devices.

The valve assembly discussed above may be constructed from a minimum number of components. Preferably, only the valve head and the housing need to be moulded as separate components. Once fitted together these two components will form the completed valve assembly.

In a preferred embodiment the housing and valve head are configured so that the valve head may be "snap fitted" into the housing and retained in place within the four engagement indentations. This "snap fitting" assembly allows a valve assembly to be constructed from two elements only, and does not require additional retaining or fixing components to be incorporated into the device.

A valve assembly configured as described above reduces the manufacturing costs by eliminating the number of tools required to manufacture the present invention and also decreases the manufacturing and assembly time for the valve assembly.

BRIEF DESCRIPTION OF DRAWINGS

Further aspects of the present invention will become apparent from the ensuing description that is given by way of example only and with reference to the accompanying drawings in which.

BEST MODES FOR CARRYING OUT THE INVENTION

Figure 1:
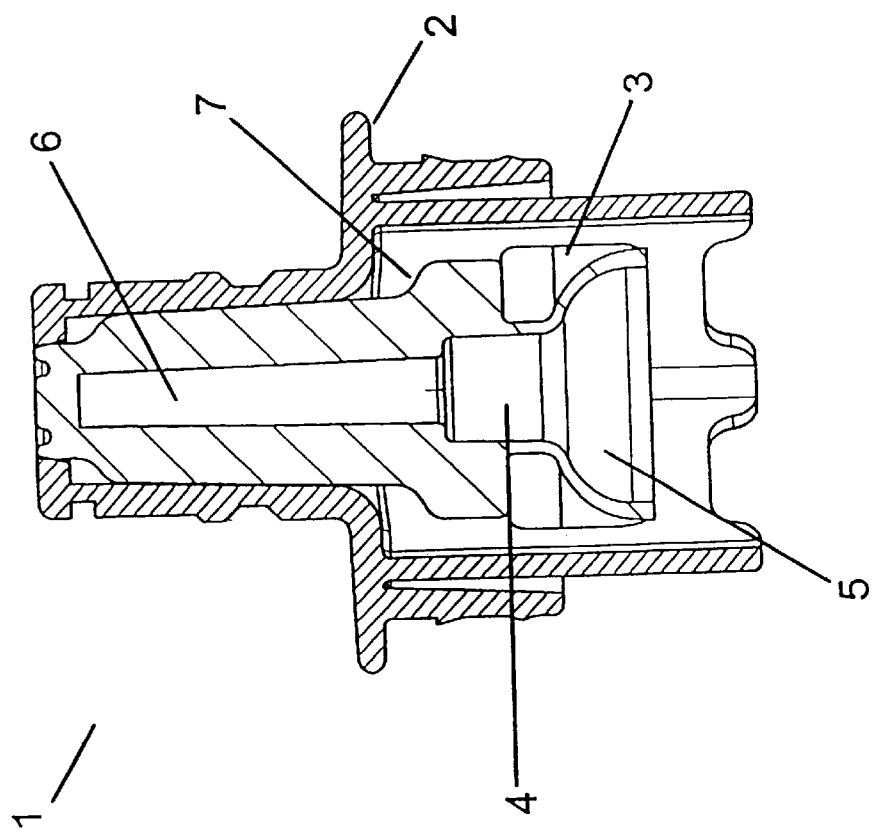
FIG. 1 illustrates a cross-sectional view of the valve assembly with the valve head inserted within the housing as in one embodiment.

FIG. 1 illustrates a cross-sectional view of the present invention as in one embodiment.

FIG. 1 shows a cross-sectional view of a valve assembly 1. The valve assembly 1 includes a housing 2, a number of engagement indentations 3 located within the housing 2, and a valve head 4.

The valve head 4 consists of an elastically deformable cup 5 and a stem 6. Associated with the valve head stem 6 are protrusions 7 that limit the travel of the valve head 4 down the body of the valve assembly housing 2.

As can be seen from FIG. 1 the valve head cup 5 is locked in place inside the engagement indentations 3.

When in use the valve stem 6 is driven into the housing 2 causing the cup 5 to run into the edges of each indentation 3.

The force applied to the valve head stem 6 will cause the cup 5 to deform when it runs up against the edges of the indentations 3. When the cup 5 deforms fluid from a fluid port above the cup 5 (not shown) can then flow past the deformed sides of the cup and out the channel located within the housing 2 in which the valve stem 6 lies.

Once the force applied to the valve stem 6 is removed the cup 5 will slide back down into its original position within the housing and will resiliently reform back into its original shape.

Figure 2:
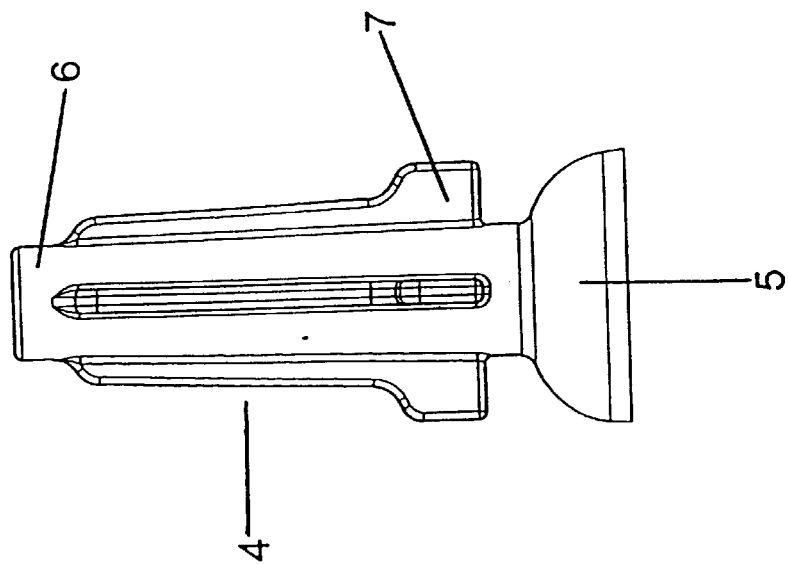
FIG. 2 illustrates the valve head as configured in the same embodiment of the present invention and shown in FIG. 1.

FIG. 2 illustrates a perspective view of the valve head 4 employed in FIG. 1.

As in FIG. 1 the valve head 4 includes a cup portion 5 a stem 6 and a number of protrusions 7.

As can be seen from the diagram the valve head 6 includes four protrusions 7 which help to locate the valve head 4 within the valve assemblies housing (not shown).

Figure 3:
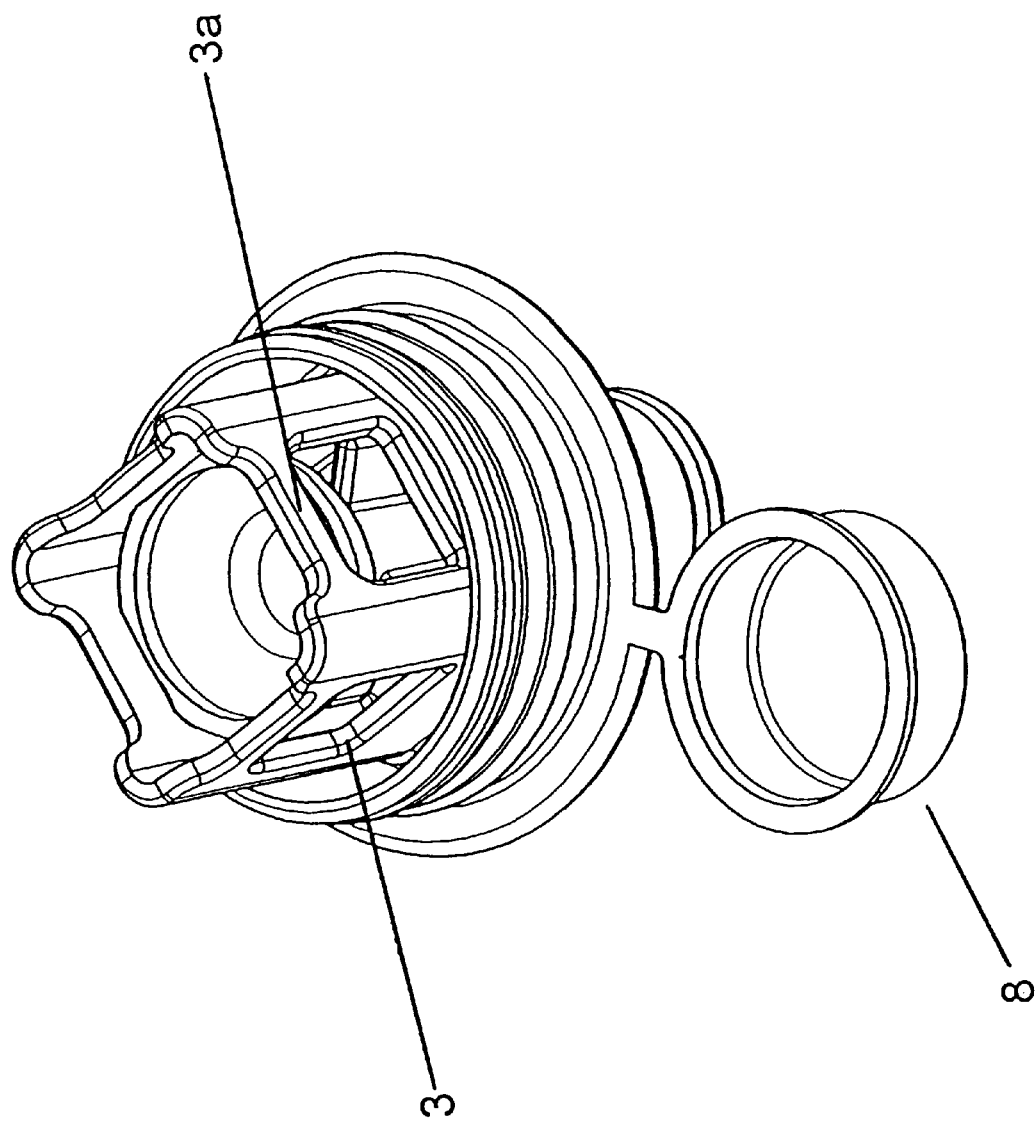
FIG. 3 illustrates a perspective view of the valve assembly housing employed in FIG. 1 and FIG. 2.

FIG. 3 illustrates a perspective view of the valve assembly housing 4.

As can be clearly seen from this view the housing 2 includes a number of engagement indentations 3 into which the edges of a valve head cup (not shown) may be retained. In use, the top edges 3a of the indentation 3 may catch the upper edge of the valve head cup when it is pushed forward, deforming the valve head cup and creating a fluid path through the valve assembly.

Also associated with the housing 2 is a cap portion 8. The cap portion 8 is attached as an integral part of the housing 2 but may be detached when required to cover the valve head stem end of the valve assembly.

Aspects of the present invention have been described by way of example only and it should be appreciated that modifications and additions may be made thereto without departing from the scope thereof as defined in the appended claims.

What we claim is:

1. A method of opening a valve assembly, comprising the steps of:
    (a) forcing a valve head against at least one engagement element by applying a force at one end of the valve head;
    (b) deforming at least a portion of the valve head located at an end of the valve head opposite said one end against the engagement element; and
    (c) creating a fluid path through the valve assembly, around the deformed valve head.

2. A valve assembly, comprising
    a housing;
    at least one engagement element integrally formed in the housing and having a stopper; and
    a valve head adapted to be received within the housing and to engage with the at least one engagement element, wherein the valve head is mounted on an end of a substantially straight stem;
    wherein the valve head assumes a closed position when no fluid path is created through the valve assembly, and an open position when the valve head is driven toward the engagement element by forces applied to the stem so that a portion of the valve head located opposite the valve stem contacts against the stopper and is thereby deformed to create a fluid path through the valve assembly around the deformed valve head.

3. The valve assembly as claimed in claim 2, wherein the valve head is formed from an elastically deformable cup mounted on the end of the substantially straight stem.

4. The valve assembly as claimed in claim 3, wherein the elastically deformable cup is made of an elastic and resilient material.

5. The valve assembly as claimed in claim 2, wherein the housing includes a central hollow channel which forms a part of the fluid path.

6. The valve assembly as claimed in claim 2, wherein the at least one engagement element comprises an indentation formed in an inner surface of the housing.

7. The valve assembly as claimed in claim 5, wherein the valve assembly includes four engagement indentations formed in an inner surface of the housing and evenly positioned around a circumference of the central hollow channel.

8. The valve assembly as claimed in claim 6, wherein the indentation comprises either of a recess and an aperture.

9. The valve assembly as claimed in claim 6, wherein the valve head is adapted to be snap-fitted into the housing and to be firmly retained within the indentation.

10. The valve assembly as claimed in claim 9, wherein the valve head includes an elastically deformable cup having a cup edge adapted to sit inside the indentation.

11. The valve assembly as claimed in claim 10, wherein the stopper comprises a forward edge of the indentation which the cup edge rests against when the valve head is driven toward the engagement element.

12. A valve assembly, comprising a housing;

at least one engagement element integrally formed in the housing and having a stopper; and a valve head adapted to be received within the housing and to engage with the at least one engagement element, wherein the valve head is formed from an elastically deformable cup mounted on an end of a substantially straight stem;

wherein the valve head assumes a closed position when no fluid path is created through the valve assembly, and an open position when the valve head is driven to rest against the stopper and deformed, to thereby create a fluid path through the valve assembly, around the deformed valve head, wherein the stem includes a plurality of protrusions along its length to limit movements of the valve head along an axis of the housing.

* * * * *